(12) United States Patent
Kremeier (10) Patent No.: US 12,133,953 B2
(45) Date of Patent: Nov. 5, 2024

(54) RESPIRATORY DEVICE

(71) Applicant: Loewenstein Medical Technology S.A., Luxembourg (LU)

(72) Inventor: Peter Kremeier, Karlsruhe (DE)

(73) Assignee: LOEWENSTEIN Medical Technology S.A., Luxembourg (LU)

( * ) Notice: Subject to any disclaimer, the term of this patent is extended or adjusted under 35 U.S.C. 154(b) by 601 days.

(21) Appl. No.: 16/579,966

(22) Filed: Sep. 24, 2019

(65) Prior Publication Data

US 2020/0094006 A1 Mar. 26, 2020

(30) Foreign Application Priority Data

Sep. 26, 2018 (DE) .......................... 102018007602.5

(51) Int. Cl.
*A61M 16/00* (2006.01)
*A61B 5/08* (2006.01)
(Continued)

(52) U.S. Cl.
CPC ......... *A61M 16/024* (2017.08); *A61B 5/0809* (2013.01); *A61B 5/0833* (2013.01);
(Continued)

(58) Field of Classification Search
CPC ............. A61M 16/00; A61M 16/0066; A61M 16/0069; A61M 16/024;
(Continued)

(56) References Cited

U.S. PATENT DOCUMENTS

| 6,079,412 A | * | 6/2000 | Meier | ................. | A61M 16/024 128/204.18 |
| 2008/0295839 A1 | * | 12/2008 | Habashi | ............ | A61M 16/0069 128/204.22 |

(Continued)

FOREIGN PATENT DOCUMENTS

| DE | 19716166 A1 | 10/1998 |
| DE | 10301202 B3 | 1/2004 |

(Continued)

*Primary Examiner* — Joseph D. Boecker
(74) *Attorney, Agent, or Firm* — Abel Schillinger, LLP (57) ABSTRACT

A respiratory device comprises a respirator having a controllable respiratory gas source, a programmable control unit and at least one sensor unit for determining pressure and/or flow of respiratory gas. The control unit controls a respiratory gas source to specify a first respiration pattern. The respiratory device comprises at least two further sensor units, a first sensor unit comprising a plurality of individual sensors for generating and/or measuring electrical potentials and noninvasively determining the electrical impedance of the lungs of a patient, a second sensor unit for noninvasively determining the carbon dioxide supply and a third sensor unit for noninvasively determining the oxygen supply of the patient. The control unit evaluates the measured values of the first, second and third sensor units to determine the instantaneous ventilation of the lungs during the respiration using the first respiration pattern, the instantaneous carbon dioxide supply and the instantaneous oxygen supply.

18 Claims, 4 Drawing Sheets

(51) Int. Cl.
*A61B 5/083* (2006.01)
*A61M 16/06* (2006.01)

(52) U.S. Cl.
CPC ............ *A61B 5/0836* (2013.01); *A61M 16/06* (2013.01); *A61M 2016/0027* (2013.01); *A61M 2016/0033* (2013.01); *A61M 2205/3334* (2013.01); *A61M 2205/3344* (2013.01); *A61M 2205/52* (2013.01); *A61M 2230/432* (2013.01); *A61M 2230/435* (2013.01); *A61M 2230/65* (2013.01)

(58) Field of Classification Search
CPC .. A61M 2016/0018; A61M 2016/0027; A61M 2016/0033; A61M 2230/432; A61M 2230/435; A61M 2230/65; A61B 5/0536; A61B 5/0809; A61B 5/0833; A61B 5/0836
See application file for complete search history.

(56) References Cited

U.S. PATENT DOCUMENTS

| | | | |
|---|---|---|---|
| 2015/0379706 A1* | 12/2015 | Leonhardt | G01R 33/56366 |
| | | | 382/131 |
| 2016/0008561 A1 | 1/2016 | Novotni et al. | |
| 2018/0280646 A1* | 10/2018 | Freeman | A61M 16/0003 |
| 2019/0125277 A1* | 5/2019 | Radke | A61B 5/0536 |
| 2020/0016352 A1* | 1/2020 | Stender | A61B 5/0816 |
| 2021/0267480 A1* | 9/2021 | Wi | A61B 5/318 |

FOREIGN PATENT DOCUMENTS

| | | |
|---|---|---|
| DE | 102013203177 A1 | 8/2014 |
| DE | 102016107603 A1 | 10/2017 |

\* cited by examiner

RESPIRATORY DEVICE

CROSS-REFERENCE TO RELATED APPLICATIONS

The present application claims priority under 35 U.S.C. § 119 of German Patent Application No. 10 2018 007 602.5, filed on Sep. 26, 2018, the entire disclosure of which is expressly incorporated by reference herein.

BACKGROUND OF THE INVENTION

1. Field of the Invention

The present invention relates to a respiratory device.

2. Discussion of Background Information

In the event of respiratory insufficiency, the reduced ventilation of the lungs results in a reduced oxygen absorption and in some cases also in an elevated carbon dioxide content in the tissue. This results in change of the blood gas values. In principle, disturbances of the oxygenation are to be differentiated from disturbances of the ventilation. In the case of disturbances of the oxygenation, the oxygen partial pressure in the blood can sink while the body can still compensate for the carbon dioxide partial pressure. In the case of disturbances of the ventilation, oxygen partial pressure and carbon dioxide partial pressure can be changed.

One method for determining the ventilation of the lungs is electrical impedance tomography (EIT). In electrical impedance tomography (EIT), weak alternating currents flow on paths of least resistance through the body and generate electrical potentials on the surface at the same time. The measured surface potentials are dependent on the impedance (resistance) distribution within the thorax. The measured resistance is predominantly determined by the intra-pulmonary air content. Because of the high time resolution, the method offers the option of detecting rapid physiological changes. For example, the respirator elisa 800 VIT (SALVIA medical GmbH & Co. KG, Niederhöchstadter Str. 62, 61476 Kronberg, Germany) uses the EIT technology.

Less ventilated lung areas may be identified using the EIT technology.

According to the prior art, EIT data can be used by the physician to judge the ventilation of the lungs.

The effects of a change of the artificial ventilation on the oxygen supply and the carbon dioxide content, in particular the oxygen partial pressure and the carbon dioxide partial pressure, are clinically not taken into consideration sufficiently when setting the respiration.

It would therefore be advantageous to provide a respiratory device in which items of information about the ventilation of the lungs and items of information about the oxygen supply and the carbon dioxide content are used for the control or regulation, which is automatic, for example, of the respiration.

SUMMARY OF THE INVENTION

The present invention provides a respiratory device, which comprises at least one respirator having at least one controllable respiratory gas source and a programmable control unit and at least one sensor unit for determining pressure and/or flow of the respiratory gas, wherein the control unit controls the respiratory gas source to specify a first respiration pattern (with respect to pressure, flow, volume, frequency) and the respiratory device comprises at least two further sensor units, wherein one sensor unit comprises a plurality of individual sensors which are designed for generating and/or measuring electrical potentials and are designed for noninvasively determining the electrical impedance (EI) of the lungs of a patient. The second sensor unit is designed for noninvasively determining the carbon dioxide supply and the third sensor unit is designed for noninvasively determining the oxygen supply of the patient. The control unit evaluates the sensor measured values of the EI sensor unit to determine the instantaneous ventilation of the lungs during the respiration using the first respiration pattern, evaluates the sensor measured values of the second sensor unit to determine the instantaneous carbon dioxide supply, and evaluates the sensor measured values of the third sensor unit to determine the instantaneous oxygen supply.

The respiratory device may also be characterized in that the control unit controls the respiratory gas source to specify a first respiration pattern and stores the resulting first sensor (measured) values of at least one sensor unit, wherein the control unit then controls the respiratory gas source to specify a second respiration pattern and stores the resulting second sensor (measured) values of at least one sensor unit and compares the first sensor (measured) values to the second sensor measured values.

The respiratory device may also be characterized in that the respiratory device comprises at least one storage unit communicating with the control unit, in which at least standard values and/or limiting values for the carbon dioxide supply and for the oxygen supply are stored.

The respiratory device may also be characterized in that the control unit controls the respiratory gas source to specify a second respiration pattern, which is different from the first respiration pattern with respect to pressure and/or flow and/or volume and/or frequency, if the sensor measured values of the instantaneous carbon dioxide supply and/or the sensor measured values of the instantaneous oxygen supply deviate from the standard values and/or limiting values are at least reached.

The respiratory device may also be characterized in that standard values and limiting values for the ventilation of the lungs are stored in the storage unit and the control unit controls the respiratory gas source to specify a second respiration pattern, which is different from the first respiration pattern with respect to pressure and/or flow and/or volume and/or frequency, if the instantaneous ventilation deviates from the standard values and limiting values are at least reached.

The respiratory device may also be characterized in that the control unit evaluates the sensor measured values of the EI sensor unit to determine the resulting ventilation of the lungs during the respiration using the second respiration pattern, wherein the control unit evaluates the sensor measured values of the second sensor unit to determine the resulting carbon dioxide supply during the respiration using the second respiration pattern and evaluates the sensor measured values of the third sensor unit to determine the resulting oxygen supply during the respiration using the second respiration pattern and wherein the control unit compares the instantaneous ventilation to the resulting ventilation.

The respiratory device may also be characterized in that the control unit controls the respiratory gas source to specify a second respiration pattern in such a way that the resulting ventilation of the lungs is improved in relation to the instantaneous ventilation.

The respiratory device may also be characterized in that the control unit controls the respiratory gas source to specify a second respiration pattern, which is different from the first respiration pattern with respect to pressure and/or flow and/or volume and/or frequency, so that the sensor measured values of the resulting carbon dioxide supply or oxygen supply at least approximate target values.

The respiratory device may also be characterized in that the control unit controls the respiratory gas source to specify a second respiration pattern, which is different from the first respiration pattern with respect to pressure and/or flow and/or volume and/or frequency, if the sensor measured values of the instantaneous ventilation and/or the sensor measured values of the instantaneous oxygen partial pressure deviate from the standard values and limiting values are at least reached.

The respiratory device may also be characterized in that the control unit controls the respiratory gas source to specify a second respiration pattern, which is different from the first respiration pattern with respect to pressure and/or flow and/or volume and/or frequency, if the sensor unit identifies an unchanged EIT summation signal and a high or elevated EIT change frequency, wherein the second respiration pattern has an elevated mandatory frequency in comparison to the first respiration pattern.

The respiratory device may also be characterized in that the control unit controls the respiratory gas source to specify a second respiration pattern, which is different from the first respiration pattern with respect to pressure and/or flow and/or volume and/or frequency, if the sensor unit comprises an EIT summation signal unchanged in comparison to the first respiration pattern and a reduced amount for the carbon dioxide supply, wherein the second respiration pattern has an elevated mandatory frequency in comparison to the first respiration pattern.

The respiratory device may also be characterized in that the control unit controls the respiratory gas source to specify a second respiration pattern, which is different from the first respiration pattern with respect to pressure and/or flow and/or volume and/or frequency, if the sensor unit comprises an EIT summation signal reduced in comparison to the first respiration pattern and a reduced amount for the carbon dioxide supply, wherein the second respiration pattern has an elevated mandatory frequency in comparison to the first respiration pattern and/or an elevated tidal volume and/or an elevated pressure assistance.

The respiratory device may also be characterized in that the control unit controls the respiratory gas source to specify a second respiration pattern, which is different from the first respiration pattern with respect to pressure and/or flow and/or volume and/or frequency, if the sensor unit comprises an unchanged EIT summation signal and an elevated amount for the carbon dioxide supply, wherein the second respiration pattern has an EPAP pressure or course which is changed in comparison to the first respiration pattern.

The respiratory device may also be characterized in that the control unit controls the respiratory gas source to specify a second respiration pattern, which is different from the first respiration pattern with respect to pressure and/or flow and/or volume and/or frequency, if the sensor unit comprises an EIT summation signal unchanged in comparison to the first respiration pattern and an elevated amount for the carbon dioxide supply, wherein the second respiration pattern can have an elevated mandatory frequency in comparison to the first respiration pattern if the EIT change frequency is reduced.

The respiratory device may also be characterized in that the control unit controls the respiratory gas source to specify a second respiration pattern, which is different from the first respiration pattern with respect to pressure and/or flow and/or volume and/or frequency, if the sensor unit comprises an EIT summation signal reduced in comparison to the first respiration pattern and a reduced EIT change frequency and an elevated amount for the carbon dioxide supply, wherein the second respiration pattern has an elevated mandatory frequency in comparison to the first respiration pattern and/or an elevated tidal volume and/or an elevated pressure assistance.

The respiratory device may also be characterized in that the control unit controls the respiratory gas source to specify a second respiration pattern if the sensor unit comprises an elevated EIT summation signal and/or an EIT change frequency reduced in comparison to the first respiration pattern and also a reduced amount for the oxygen supply, wherein the second respiration pattern can have an elevated frequency in comparison to the first respiration pattern and/or an at least short-term elevation of the inspiration time and/or an adaptation of the PEEP and/or a change of the respiration pattern.

The respiration device may also be characterized in that the control unit controls the respiratory gas source to specify a first PEEP and stores the resulting first sensor (measured) values of at least one sensor unit, wherein the control unit then controls the respiratory gas source to specify a second PEEP and stores the resulting second sensor (measured) values of at least one sensor unit, wherein the control unit then compares the first sensor (measured) values to the second sensor measured values.

The respiratory device may also be characterized in that the control unit controls the respiratory gas source to specify a first respiration pattern, in which the EPAP pressure has a first value or a first course, wherein the sensor unit for noninvasively determining the electrical impedance (EI) determines the resulting ventilation of the lungs and wherein the second sensor unit determines the carbon dioxide supply and/or wherein the third sensor unit determines the oxygen supply of the patient, wherein the control unit stores the sensor measured values which result during the respiration using the first pattern, wherein the control unit controls the respiratory gas source to specify a second respiration pattern, in which the EPAP pressure has a second value or a second course, wherein the sensor unit for noninvasively determining the electrical impedance (EI) determines the resulting ventilation of the lungs and wherein the second sensor unit determines the carbon dioxide supply and/or wherein the third sensor unit determines the oxygen supply of the patient, wherein the control unit stores the sensor measured values which result during the respiration using the second pattern, and wherein the control unit compares the sensor measured values which result after application of the first respiration pattern to the sensor measured values which result after application of the second respiration pattern, and/or displays them for comparison on the display screen.

The respiratory device may also be characterized in that the control unit monitors at least one sensor signal for errors in that if an instantaneous sensor signal reaches limiting values, it is compared to another instantaneous sensor signal to detect an inaccuracy.

The respiratory device may also be characterized in that the control unit monitors an EIT sensor signal for errors in that the control unit at least temporarily compares the EIT sensor signal to the sensor signal of a sensor unit for determining pressure and/or flow of the respiratory gas.

The respiratory device may also be characterized in that the control unit monitors an EIT sensor signal for errors in that the control unit compares the EIT sensor signal to a modeled sensor signal.

The respiratory device may also be characterized in that the modeled sensor signal is essentially continuously learned.

The device according to the invention helps to detect respiratory complications early and avoid them. Resulting costs are thus prevented. In-clinic transportations, which are costly and subject to complications, of intensive care patients requiring respiration are reduced. At every point in time, a differentiated statement on the ventilation of the lungs and the supply with oxygen and/or carbon dioxide is possible.

A differentiated judgment of the ventilation was heretofore only possible as a snapshot using imaging methods (for example, thorax CT). The ventilation can be continuously analyzed and monitored using the new technology. By overlaying the lung contours of the patient, spatial ventilation distributions can be assigned and therapeutically evaluated. The representation is noninvasive, high-resolution, and takes place in real time.

Using the device according to the invention, the situation of the lungs can be judged in real time and the effects of the adaptation of the respiration settings can be progressively judged. Respiratory cycle collapse areas and distention regions are identifiable and can be evaluated.

Further advantages and features of the present invention result from the description of the exemplary embodiments, which are explained hereafter with reference to the appended figures.

BRIEF DESCRIPTION OF THE DRAWINGS

Preferred exemplary embodiments of the invention are explained in greater detail hereafter on the basis of schematic illustrations. In the drawings.

DETAILED DESCRIPTION OF EXEMPLARY EMBODIMENTS

The particulars shown herein are by way of example and for purposes of illustrative discussion of the embodiments of the present invention only and are presented in the cause of providing what is believed to be the most useful and readily understood description of the principles and conceptual aspects of the present invention. In this regard, no attempt is made to show details of the present invention in more detail than is necessary for the fundamental understanding of the present invention, the description in combination with the drawings making apparent to those of skill in the art how the several forms of the present invention may be embodied in practice.

Figure 1:
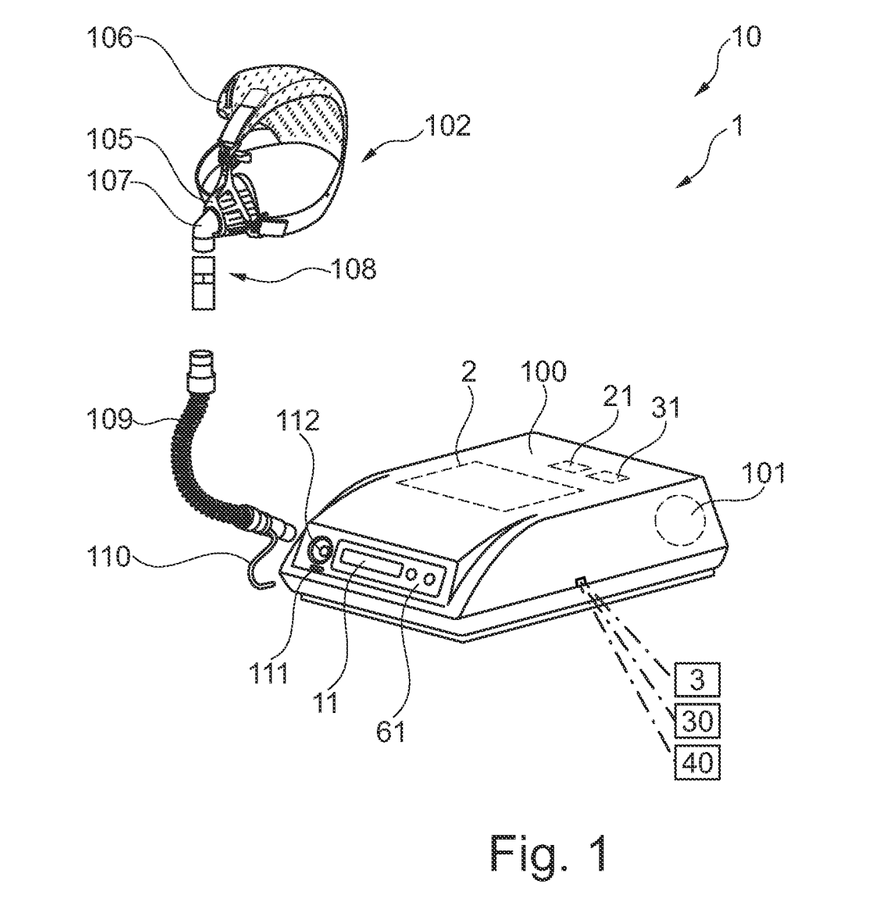
FIG. 1 shows a respiratory device according to the invention.

FIG. 1 shows a respiratory device 10 according to the invention, which is embodied here as a home respirator or sleep therapy device or clinical respirator. The respirator 1 and the respiratory device 10 are designed to carry out the method according to the invention.

The respiratory device (10) comprises at least one respirator (1) having at least one controllable respiratory gas source (100) and a programmable control unit (21) and at least one sensor unit (2) for determining pressure and/or flow of the respiratory gas, wherein the control unit (21) controls the respiratory gas source to specify a first predetermined respiration pattern (with respect to pressure, flow, volume, frequency). The respiratory device (10) moreover comprises at least two further sensor units (3, 30, 40), which are spatially separated from the respirator (1), and which communicate with the control unit (21) of the respiratory device (10). One sensor unit (3) comprises a plurality of individual sensors (3, 3', 3'' . . . ) and each sensor unit is designed to generate electrical potentials and/or to noninvasively determine the electrical impedance (EI) of a body section and to ascertain and transmit the sensor measured values to the control unit. The programmable control unit (21) evaluates the sensor measured values of the EI sensor unit (3) to determine the instantaneous ventilation of the lungs during the respiration using the first respiration pattern. The control unit (21) also controls the respiratory gas source, for example, to specify a second respiration pattern, which is different from the first respiration pattern with respect to pressure and/or flow and/or volume and/or frequency, wherein the control unit (21) evaluates the sensor measured values of the EI sensor unit (3) to determine the resulting ventilation of the lungs during the respiration using the second respiration pattern and the control unit (21) compares the instantaneous ventilation to the resulting ventilation to establish the better suitable respiration pattern. Wherein a user can make specifications to predetermine target values which have to be reached to achieve a "better suitable respiration pattern". Wherein alternatively or additionally changes of the carbon dioxide and/or oxygen measured values are also an important criterion which are significant in the decision upon the selection or the continuance of respiration patterns.

The respirator 1 comprises a respiratory gas source 100 having, for example, a blower unit and/or a valve unit 101 for generating an airflow for the respiration. A control unit 21 is provided here for controlling the respiratory gas source 100 for acquiring and processing sensor data. The operation and setting of the respirator 1 take place via a user interface 61 having operating elements and a display unit 11 (display screen).

The respirator 1 comprises a respiration interface 102 to supply the airflow to a patient for respiration. The respiration interface 102 shown here is a respiration mask 105 designed by way of example as a nasal mask. A hood 106 is provided for fixing the respiration mask 105, for example. The respiration interface 102 can also be embodied, for example, as a full-face mask, as a nasal cannula, as a tube, or as a larynx mask.

At least one connecting hose 109, which is connected to the respiratory gas source 100 via a coupling unit 112 to conduct air, is provided for connecting the respiration interface 102 to the respiratory gas source 100. The connecting hose 109 is connected to the respiration interface 102 via a coupling element 107. An exhalation element 108, which comprises a valve or is formed as such, is arranged between the connecting hose 109 and the coupling element 107. The exhalation element 108 is provided, for example, to prevent a respiration back into the respirator 1 during the exhalation of the user.

The control unit 21 is connected to a sensor unit (2, 3, 30, 40) (not shown in greater detail), which comprises one or more sensors for acquiring device parameters and/or patient parameters and/or other variables characteristic for the respiration. The control unit 21 can be embodied as a central control unit, for example, in the respirator, which processes all sensor values. The control unit 21 can be embodied in the form of multiple decentralized control units, for example, one in the respirator and one (each) associated with the one (or the) sensor(s).

For example, the control unit 21 comprises a pressure sensor (2) (not shown in greater detail here), which ascertains the pressure conditions of the respiratory gas. For this purpose, the pressure sensor is operationally connected to the respiratory gas, for example, via a pressure measuring hose 110 to the respiration interface 102. The pressure measuring hose 110 is connected to the control unit 21 via an inlet nozzle 111. For example, the control unit 21 also comprises a flow sensor (2) (not shown in greater detail here), which ascertains the flow conditions of the respiratory gas.

Furthermore, the control unit 21 is used here to control the blower unit and/or the valve unit 101. The control unit 21 provides a required minimum pressure and compensates for pressure variations, which are caused by the respiratory activity of the user. For example, the control unit 21 also acquires the present pressure in the respiration mask 105 (or the patient interface) and adjusts the output of the respiratory gas source accordingly until a desired respiration pressure is applied.

The device parameters required for setting the respiratory gas source 100 and the device configuration and/or device software are stored in a storage unit 31.

The control unit 21 can also regulate the oxygen content in the respiratory gas by corresponding control of the blower unit and/or the valve unit 101, wherein the valve unit comprises or connects at least one oxygen source (pressurized gas bottle or hospital line). The oxygen admixture to the respiratory gas flow takes place downstream or upstream from the blower unit, for example. In this case, the valve unit is an oxygen mixing valve. The oxygen admixture to the respiratory gas flow takes place, for example, by way of a valve unit, which guides and regulates the respiratory gas flow and the oxygen flow.

The control unit 21 can also be designed for acquiring sensorially acquired patient parameters. The control unit 21 can be equipped for this purpose with sensors for measuring the respiratory excursion, for measuring an oxygen supply and/or a carbon dioxide supply, and/or for measuring an EEG, an EMG, an EOG, or an ECG activity.

The respiratory device comprises in particular at least two sensor units (3, 30, 40), which are spatially separated from the respirator (1) and communicate with the control unit (21), wherein a sensor unit (3) comprises a plurality of individual sensors (3, 3, 3" . . . ) and each sensor unit is designed for generating electrical potentials (13) for noninvasively determining the electrical impedance (EI) of a body section. The sensor units (3) are embodied, for example, as an adhesive bandage, having an outer layer facing away from the skin and an adhesive layer facing toward the skin, or assembled as a belt, which holds the sensor units.

The respiratory device (10) comprises at least one further sensor unit (30), which is designed for noninvasively determining the $CO_2$ (30). The sensor unit (30) is embodied, for example, as a clamp sensor or as an adhesive bandage having an outer layer facing away from the skin and an adhesive layer facing toward the skin. The respiratory device (10) comprises at least one further sensor unit (40), which is designed for noninvasively determining the $O_2$ (40). The sensor unit (30) is embodied, for example, as a clamp sensor or as an adhesive bandage having an outer layer facing away from the skin and an adhesive layer facing toward the skin.

The sensor units (3, 30, 40) comprise, for example, energy and transmission means for the ascertainment and wireless transmission of the sensor measured values. The sensor units (3, 30, 40) alternatively comprise, for example, communication means (35, 45) for transmitting the sensor measured values to the controller (21).

Figure 2:
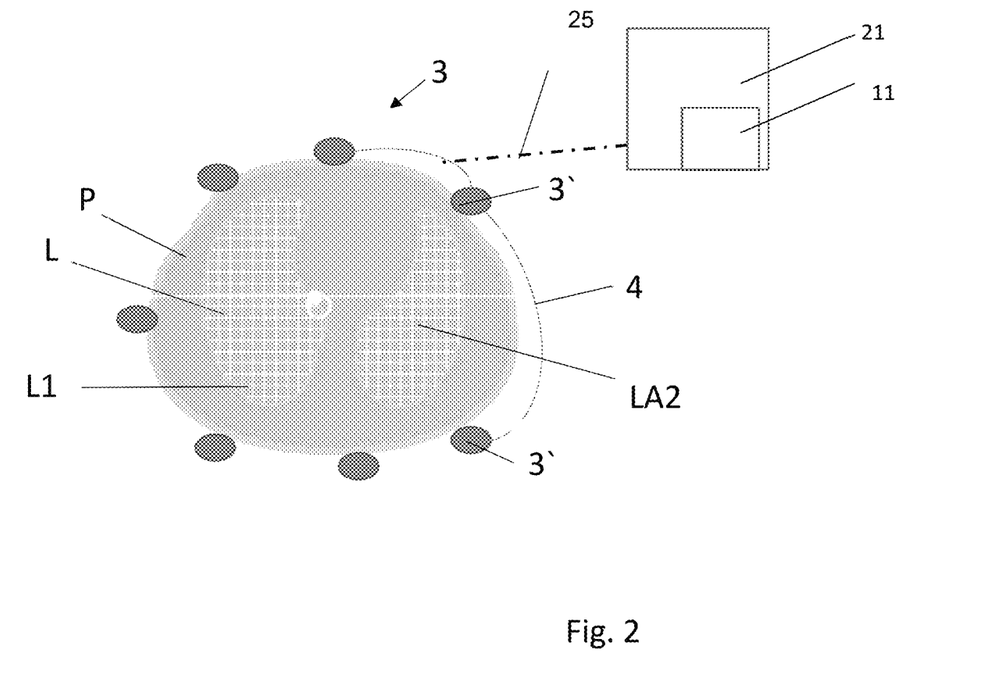
FIG. 2 shows a schematic representation of the EIT measurement on the display screen of the respiratory device.

FIG. 2 shows a schematic illustration of the EIT measurement. The sensor unit (3) comprises a plurality of individual sensors (3, 3', 3" . . . ), which are designed for generating and/or measuring electrical potentials and are used for noninvasively determining the electrical impedance (EI) of the lungs (L) of a patient (P).

The sensor unit comprises, for example, 32 high-resolution sensors (3, 3' . . . ) in a textile belt (not shown). An integrated location sensor (not shown here) determines the position of the patient. The sensors are connected to one another by communication or conduction means (4) and are arranged so that they can receive signals in succession from all directions. The control unit (21) can therefore spatially assign the sensor measured values of the EIT measurement (3). Therefore, the local tissue resistances can be ascertained from different directions and then converted into moving images. The control unit (21) processes the sensor measured values of the EIT measurement (3) in such a way that a specific electrical impedance (EI) is ascertained for individual lung sections (LA1, LA2). The sensor unit (3) is connected via wired or wireless communication means (25) to the control unit (21). The control unit (21) stores (11) and processes the sensor measured values for use in the respiratory device. The storage unit (31) can be part of the control unit (21) or a separate component.

FIG. 2 also shows a schematic illustration of the results of the EIT measurement on the display screen of the respiratory device. The control unit (21) processes the sensor measured values for use in the respiratory device in such a way that a visualization of the patient thorax (P) having the two lungs (L) is represented on the display screen of the respiratory device (10). The control unit (21) processes the sensor measured values of the EIT measurement (3) in such a way that a specific electrical impedance (EI) of the lungs (L) is ascertained for individual lung sections (LA1, LA2). The specific electrical impedance (EI) of the lung sections (LA) is prepared for the representation on the display screen in such a way that lung sections having a high electrical impedance (L2) are graphically represented differently than those lung sections having a low electrical impedance (L1). The control unit (21) processes the sensor measured values of the EIT measurement (3) with respect to time in such a way that a specific electrical impedance (EI) of the lungs (1) is ascertained breath by breath for individual lung sections (LA1, LA2) and prepared for the representation on the display.

The sensor unit (3) is also configured and designed (together with the controller and the storage unit) to form an EIT summation signal (44'), which is a measure of the ventilation of the lungs or of lung sections. The sensor unit (3) is also configured and designed (together with the controller and the storage unit) to ascertain a frequency of the EIT change frequency (44"). The sensor unit (3) can thus in summary ascertain the instantaneous ventilation (44).

In the meaning of the invention, the EIT summation signal (44') is understood to mean that the impedance distribution or impedance change distribution in the sectional plane defined by the sensors or the volume spanned by the sensors does not necessarily have to be visually represented on a display screen, for example, to carry out the method according to the invention, but at least the computed result values of the impedance distribution or impedance change distribution are provided in the device according to the invention (to carry out the method).

Upon a summation of all impedance values of the sensors, a changed summation signal accordingly results during the inspiration in comparison to the summation signal during the expiration. The summation value accordingly represents an adequate measure to determine the ventilation of the lungs.

The EIT change frequency (44″) may be determined from the change, in dependence on the respiratory phase, of the impedance values of the sensors. The impedance values of the sensors vary in dependence on the respiratory phase with the inspiration and the expiration. The EIT change frequency (44″) accordingly represents an alternative or additional measure to determine the (frequency of the) ventilation of the lungs.

The sensors are integrated, for example, into a textile and breathable and expandable electrode belt, together with a location sensor. The sensor unit (3) and the control unit are configured to generate a frame rate of, for example, up to 50 per second. In this case, lung regions (LA) are visualized. According to the invention, patient-related inputs are possible, such as body height, body weight, sex, chest circumference.

The EIT data thus ascertained and prepared enable a chronologically and spatially resolved differentiated analysis and representation of the electrical impedance (EI) of the lungs.

According to the invention, the metrology and control technology of the respiratory device are networked with the electrical impedance tomography (EIT). The function of the lungs can thus be continuously represented by imaging. The measured values of the respiratory device are combined with the results of the electrical impedance tomography. This technology thus enables greatly varying clinical questions to be evaluated and the therapy to be oriented accordingly.

The gases carbon dioxide ($CO_2$) and oxygen ($O_2$) can diffuse easily through body tissue and also through the skin. Noninvasive sensors which are applied to the skin can measure O2 and CO2 if the skin is also heated in addition to the sensor to a temperature which is above the body temperature. Due to the heat, typically 42° to 45° C., the local capillary blood flow is elevated and the gas diffusion is increased. This permits a quite precise determination of the $CO_2/O_2$ measured values on the skin surface.

Figure 3:
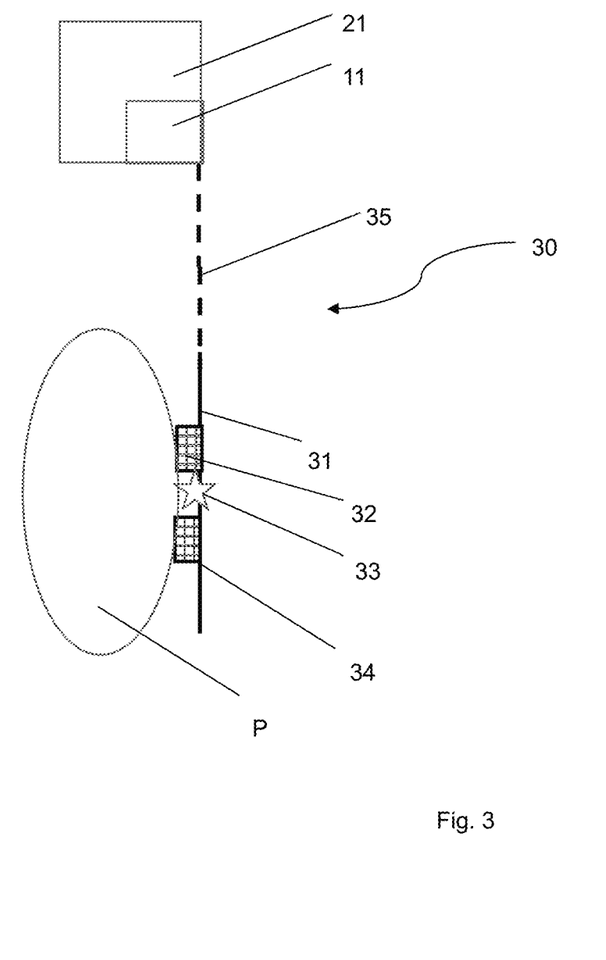
FIG. 3 shows a schematic representation of the transcutaneous blood gas analysis of the carbon dioxide potential of the skin.

FIG. 3 shows a schematic illustration of the transcutaneous blood gas analysis of tpCO2. With the aid of transcutaneous carbon dioxide measurement, the carbon dioxide potential of the skin (tpCO2) can be determined noninvasively. The measurement accuracy is less strongly dependent on the perfusion than the tpO2. The pCO2 at the skin surface is approximately 1.37 times the arterial pCO2 at 44° C. The sensor used according to the invention takes this relationship into consideration by way of a correction factor. The $pCO_2$ sensor typically warms the skin to 42° to 45° C. and uses a pH glass electrode in a thin electrolyte layer below a hydrophobic, $CO_2$- and $O_2$-permeable membrane. An evaluation unit converts the signals of the interaction at the electrode into an electrical signal and transmits it to the control unit The transcutaneous blood gas measurement enables the measurement of tpCO2 through the skin of a patient. The fundamental functionality of the sensor is illustrated in FIG. 3. The carbon dioxide diffuses out of the skin of the patient (P) into the sensor element (32, 34). The sensor comprises at least one sensor element (32, 34), which is sensitive to carbon dioxide; two or more sensor elements (32, 34) can also be used. A heat source (33) ensures warming (42-45° C.) of the skin of the patient (P) who is adjacent to the sensor. The elevated temperature results in increased perfusion of the skin and the capillary bed. Carbon dioxide is thus increasingly released. The sensor has a response time in the range of seconds to minutes. The sensor enables a stable operation of at least 5 hours without signal drift. The sensor unit (30) is connected via wired or wireless communication means (35) to the control unit (21). The control unit (21) stores (11) and processes the sensor measured values for use in the respiratory device. The storage unit (31) can be part of the control unit (21) or a separate component.

The sensor unit (30) is configured and designed (together with the control unit (21) and the storage unit) to form an instantaneous amount (46) for the carbon dioxide supply, for example, the carbon dioxide partial pressure.

Figure 4:
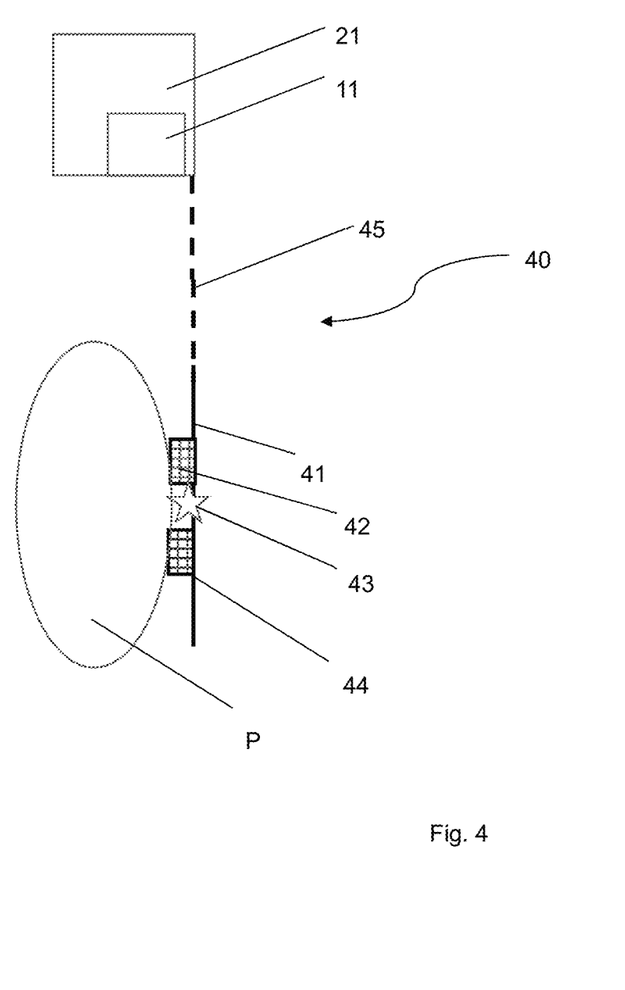
FIG. 4 shows a schematic representation of the transcutaneous blood gas analysis of pO2.

FIG. 4 shows a schematic illustration of the transcutaneous blood gas analysis of pO2. The oxygen potential of the skin (tpO2) can be determined noninvasively with the aid of the transcutaneous oxygen measurement. The measurement accuracy is dependent on the perfusion. If a measurement is made in the same arterial supply region, a close correlation exists between tpO2 and the arterial oxygen pO2. An exemplary sensor contains fluorescent pigments in the sensor surface. The oxygen molecules interact with the fluorescent pigments. An evaluation unit converts the signals of the interaction into an electrical signal and transmits it to the control unit.

The transcutaneous blood gas measurement enables the measurement of pO2 through the skin of a patient. The fundamental functionality of the sensor is illustrated in FIG. 4. Oxygen diffuses out of the skin of the patient (P) into the sensor (42, 44). The sensor comprises at least one sensor element (42, 44), which is sensitive to oxygen; two or more sensor elements (42, 44) can also be used. A heat source (43) ensures warming (42-45° C.) of the skin of the patient (P), who is adjacent to the sensor. The elevated temperature results in increased perfusion of the skin and the capillary bed. O2 is thus increasingly released. The sensor has a response time in the range of seconds to minutes. The sensor enables a stable operation of at least 5 hours without signal drift. The sensor unit (40) is connected via wired or wireless communication means (45) to the control unit (21). The control unit (21) stores (11) and processes the sensor measured values for use in the respiratory device. The storage unit (41) can be part of the control unit (21) or a separate component.

Pulse oximetry is a further noninvasive method for measuring the arterial oxygen saturation of the blood. Established systems use two wavelengths to differentiate between oxygenated and deoxygenated blood. The signals are acquired by conducting red and infrared light through a capillary bed (finger or earlobe) and measuring the changes of the light absorption during the pulse cycle. The sensor uses red and infrared light-emitting diodes (LEDs), which emit light through the capillary bed to a photodiode. The photodiode receives the light, converts it into an electrical signal, and transmits it for computation to the evaluation unit or the control unit.

The sensor unit (40) is configured and designed (together with the control unit (21) and the storage unit) to form an instantaneous amount for the oxygen supply, for example, the oxygen partial pressure.

Tables 1 and 2 show how the control unit (21) controls the respiratory gas source to specify a respiration pattern and how the control unit (21) moreover takes into consideration sensor measured values of the instantaneous carbon dioxide supply and/or the sensor measured values of the instantaneous oxygen supply for the specification of a respiration pattern. The specification of a respiration pattern can take place directly in this case, for example, in the form of control commands for the respiratory gas source. The specification of a respiration pattern can take place indirectly in this case, for example, in the form of a respiration pattern which is proposed to the caregiver or operator of the respiratory device (for example, on the display screen).

Tables 1 and 2 show how the control unit (21) controls the respiratory gas source to specify a second respiration pattern, which is different with respect to pressure and/or flow and/or volume and/or frequency from the first respiration pattern, if the sensor measured values of the instantaneous carbon dioxide supply and/or the sensor measured values of the instantaneous oxygen supply deviate from the standard values.

TABLE 1

| EIT summation signal (44') relative signal impedance 32 electrodes monitor themselves, up to 7 electrodes can be absent | frequency of the EIT change frequency (=respiratory frequency) (44") | instantaneous measure (46) of carbon dioxide partial pressure standard value partial pressure 35-45 mmHg limiting value below 35 or above 50 | specification (55) of control unit (21) to respirator (1) |
|---|---|---|---|
| unchanged | high | low | elevation of the mandatory frequency |
| low | normal | low | elevation of tidal volume, delta-P, or pressure assistance elevation of the mandatory frequency |
| unchanged | low | high | elevation of the mandatory frequency |
| low | low | high | elevation of tidal volume, delta-P or pressure assistance, elevation of the mandatory frequency |
| high | unchanged | high | reduction of the tidal volume or delta-P automatic maneuver to judge the final inspiratory distention |
| unchanged | unchanged | high | continue respiration search for causes (extra-pulmonary reason) |

Tables 1 and 2 also show how the control unit (21) controls the respiratory gas source to specify a second respiration pattern, which is different from the first respiration pattern with respect to pressure and/or flow and/or volume and/or frequency, if the sensor measured values of the instantaneous ventilation and/or the sensor measured values of the instantaneous carbon dioxide partial pressure deviate from the standard values and limiting values are at least reached.

TABLE 2

| EIT summation signal (44') | frequency of the EIT change frequency (=respiratory frequency) (44") | instantaneous amount (47) of oxygen partial pressure standard value partial pressure 75-100 mmHg limiting value below 70 or above 105 | specification of control unit (21) to respirator (1) |
|---|---|---|---|
| low | low | low | short-term elevation of O2 possibly reduce O2 again during the course elevation of tidal volume, delta-P or pressure assistance, elevation of the mandatory frequency, change of the respiration pattern |

TABLE 2-continued

| EIT summation signal (44') | frequency of the EIT change frequency (=respiratory frequency) (44") | instantaneous amount (47) of oxygen partial pressure standard value partial pressure 75-100 mmHg limiting value below 70 or above 105 | specification of control unit (21) to respirator (1) |
|---|---|---|---|
| unchanged | unchanged | low | short-term elevation of O2 PEEP adaptations |
| high | low | low | elevation of frequency elevation of inspiration time change of the respiration pattern |

Tables 1 and 2 also show how the control unit (21) controls the respiratory gas source to specify a second respiration pattern, which is different from the first respiration pattern with respect to pressure and/or flow and/or volume and/or frequency, if the sensor measured values of the instantaneous ventilation and/or the sensor measured values of the instantaneous oxygen partial pressure deviate from the standard values and limiting values are at least reached.

Table 3 shows how the control unit (21) controls the respiratory gas source to specify a second respiration pattern, which is different from the first respiration pattern with respect to pressure and/or flow and/or volume and/or frequency, so that the sensor measured values of the resulting carbon dioxide partial pressure or oxygen partial pressure reach target values.

The control unit (21) controls the respiratory gas source to specify a second respiration pattern (with respect to pressure, flow, volume, frequency), if the sensor unit (3) comprises an unchanged EIT summation signal and a high or elevated EIT change frequency, wherein the second respiration pattern can comprise an elevated mandatory frequency in comparison to the first respiration pattern.

The control unit (21) controls the respiratory gas source to specify a second respiration pattern (with respect to pressure, flow, volume, frequency), if the sensor unit (3) comprises a reduced EIT summation signal, in comparison to the first respiration pattern, and a reduced amount for the carbon dioxide supply, wherein the second respiration pattern can comprise an elevated mandatory frequency in comparison to the first respiration pattern.

The control unit (21) controls the respiratory gas source to specify a second respiration pattern if the sensor unit (3) comprises a reduced EIT summation signal, in comparison to the first respiration pattern, and a reduced amount for the carbon dioxide supply, wherein the second respiration pattern can comprise, in comparison to the first respiration pattern, an elevated mandatory frequency and/or an elevated tidal volume and/or an elevated pressure assistance.

The control unit (21) controls the respiratory gas source to specify a second respiration pattern (with respect to pressure, flow, volume, frequency), if the sensor unit (3) comprises an unchanged EIT summation signal and an elevated measure for the carbon dioxide supply, wherein the second respiration pattern comprises a changed EPAP pressure or curve in comparison to the first respiration pattern. The EPAP pressure can also comprise a first curve in this meaning, which is changed in following cycles of the respiration automatically or upon user selection.

For example, the EPAP can rise at the beginning of the exhalation and then drop or assume a maximum value or minimum value at the middle of the exhalation. Alternatively, the EPAP can also assume a maximum value at the end of the exhalation. The EPAP can also assume different pressure levels during the exhalation. The EPAP can also be applied over a longer time period.

The control unit (21) controls the respiratory gas source to specify a second respiration pattern (with respect to pressure, flow, volume, frequency), if the sensor unit (3) comprises an unchanged EIT summation signal, in comparison to the first respiration pattern, and an elevated measure for the carbon dioxide supply, wherein the second respiration pattern can comprise an elevated mandatory frequency, in comparison to the first respiration pattern, if the EIT change frequency is reduced.

The control unit (21) controls the respiratory gas source to specify a second respiration pattern, if the sensor unit (3) comprises a reduced EIT summation signal, in comparison to the first respiration pattern, and a reduced EIT change frequency and an elevated amount for the carbon dioxide supply, wherein the second respiration pattern can comprise, in comparison to the first respiration pattern, an elevated mandatory frequency and/or an elevated tidal volume and/or an elevated pressure assistance.

The control unit (21) controls the respiratory gas source to specify a second respiration pattern if the sensor unit (3) comprises an elevated EIT summation signal, in comparison to the first respiration pattern, and an unchanged EIT change frequency, and an elevated measure for the carbon dioxide supply, wherein the second respiration pattern can comprise, in comparison to the first respiration pattern, a reduced tidal volume and/or an automatic maneuver for judging the end-inspiratory distention.

The control unit (21) controls the respiratory gas source to specify a second respiration pattern (with respect to pressure, flow, volume, frequency), if the sensor unit (3) comprises a reduced EIT summation signal and/or a reduced EIT change frequency, in comparison to the first respiration pattern, and a reduced amount for the oxygen supply, wherein the second respiration pattern can comprise, in comparison to the first respiration pattern, an elevated mandatory frequency and/or an at least short-term elevation of the oxygen admixture to the respiratory gas and/or an elevation of tidal volume, delta-P, or pressure assistance and/or a change of the respiration pattern.

The control unit (21) controls the respiratory gas source to specify a second respiration pattern (with respect to pressure, flow, volume, frequency) if the sensor unit (3) comprises an unchanged EIT summation signal and/or an unchanged EIT change frequency, in comparison to the first respiration pattern, and a reduced amount for the oxygen supply, wherein the second respiration pattern can comprise, in comparison to the first respiration pattern, an elevated mandatory frequency and/or an at least short-term elevation of the oxygen admixture to the respiratory gas and/or an adaptation of the PEEP.

The control unit (21) controls the respiratory gas source to specify a second respiration pattern (with respect to pressure, flow, volume, frequency), if the sensor unit (3) comprises an elevated EIT summation signal and/or a reduced EIT change frequency, in comparison to the first respiration pattern, and a reduced amount for the oxygen supply, wherein the second respiration pattern can comprise an elevated frequency, in comparison to the first respiration pattern, and/or an at least short-term elevation of the inspiration time and/or an adaptation of the PEEP and/or a change of the respiration pattern.

TABLE 3

| Respirator controlled | Sensory monitoring of resulting carbon dioxide and/or oxygen and/or EIT |
| --- | --- |
| (Step-by-step) adjustment of the PEEP (to test out the individually required PEEP) | Until oxygen increases or remains stable without the carbon dioxide increasing |
| (Step-by-step) reduction of the inspiratory oxygen concentration | Until oxygen reaches the desired target corridor |
| (Step-by-step) adjustment of the IPAP and/or EPAP | Until oxygen increases or remains stable without the carbon dioxide increasing and/or EIT summation signal unchanged |
| (Step-by-step) adjustment of the frequency | Until oxygen increases or remains stable without the carbon dioxide increasing and/or EIT summation signal unchanged |

Table 3 is to be understood according to the invention as follows: The control unit (21) controls the respiratory gas source to specify a first PEEP and stores the resulting first sensor (measured) values of at least one sensor unit (2, 3, 30, 40). The control unit (21) controls the respiratory gas source to specify a second PEEP and stores the resulting second sensor (measured) values of at least one sensor unit (2, 3, 30, 40). The control unit (21) then compares the first sensor (measured) values to the second sensor measured values to ascertain the better suitable PEEP pressure.

This procedure can be performed to determine the ideal PEEP pressure for n different PEEP pressures.

Table 3 is to be understood in general according to the invention as follows: The control unit (21) controls the respiratory gas source to specify a first respiration pattern and stores the resulting first sensor (measured) values of at least one sensor unit (2, 3, 30, 40). The control unit (21) controls the respiratory gas source to specify a second respiration pattern and stores the resulting second sensor (measured) values of at least one sensor unit (2, 3, 30, 40).

The control unit (21) then compares the first sensor (measured) values to the second sensor measured values to ascertain the better suitable respiration pattern.

This procedure can be performed for n different respiration patterns to determine the ideal respiration pattern.

The decision of which respiration pattern is better suitable or optimal is transmitted in this case on the basis of stored or storable standard values and limiting values for at least one, preferably at least two of the sensor measured values, for example, as a proposal for the physician or user on the display screen of the device or via remote transmission to a display screen. The user can thereupon select the better suitable respiration pattern and cause it to be executed or can modify the respiration pattern still further and then cause it to be executed. Alternatively, the device itself can determine, on the basis of stored or storable standard values and limiting values for at least one, preferably at least two of the sensor measured values, which respiration pattern is better suitable and execute it.

For example, a regulation to target device parameters of the respirator is performed by the control unit 21, which have previously been sensorially (2, 3, 30, 40) ascertained on the basis of the characteristic respiration of a patient, individually computed, and established.

It is also possible that the respiratory gas source 100 is adapted dynamically and in particular depending on the respiration phase of the patient. For example, a respiration phase change can be detected on the basis of the control unit 21, so that a higher or lower pressure can be provided depending on the respiration phase. For example, the respirator reacts to specific respiratory events, for example, snoring, breath flattening, and/or obstructive pressure peaks, with corresponding settings of the device parameters.

The pressure conditions detected by the control unit 21 are stored together with further device parameters in a storage unit 31. Moreover, the pressure conditions set by the control unit 21 and/or the performed pressure adaptations are also stored as device parameters in the storage unit 31. The acquired patient parameters can also be stored in the storage unit 31. The sensor values of the sensors (2, 3, 30, 40) are also at least partially stored in the storage unit 31.

For example, a starting therapy pressure, a maximum therapy pressure, a minimum therapy pressure, and/or a target volume and/or other device parameters suitable for setting the respiratory gas source 100 can be stored as device parameters. These device parameters are retrieved by the control unit 21 from the storage unit 31 to set the respiratory gas source 100.

Furthermore, the pressure conditions and/or other device parameters and/or patient parameters acquired over the therapy time period are stored in the storage unit 31 in the scope of courses of therapy. Courses of therapy can be registered, for example, as a flow course, a pressure course, and/or an event course. The courses of therapy are provided to the storage unit 31 by the control unit 21, which acquires these data during the therapy.

The therapy data can also be read out via a display screen 11 located in the device 1 and/or connected to the device 1 and/or a user interface 61.

In some cases (ventilation insufficiency, earlier respiratory global insufficiency) having elevated $pCO_2$ values, the supply of oxygen and the exhalation of carbon dioxide is only possible with simultaneous respiration.

For example, the control unit (21) controls the respiratory gas source to specify a first respiration pattern (45), in which the EPAP pressure has a first value or a first course, wherein the sensor unit (3) for noninvasively determining the electrical impedance (EI) determines the resulting ventilation of the lungs and wherein the second sensor unit (30) determines the carbon dioxide supply and/or wherein the third sensor unit (40) determines the oxygen supply of the patient. The control unit (21) stores the sensor measured values which result during the respiration using the first pattern.

The EPAP pressure can have a first value, which is changed in following cycles of the respiration automatically or upon user selection. The change can be an increase or decrease. The goal of the change is in each case to find the EPAP pressure at which the sensor measured values (3, 30, 40) can be interpreted as an improvement of the ventilation and/or the oxygen supply.

In this meaning, the EPAP pressure can also have a first course which is changed automatically or upon user selection in following cycles of the respiration.

For example, the EPAP can rise at the beginning of the exhalation and then drop or assume a maximum value or minimum value in the middle of the exhalation. Alternatively, the EPAP can also assume a maximum value at the end of the exhalation. The EPAP can also assume different pressure levels during the exhalation.

Such a titration can also be performed for the IPAP (separately from the EPAP or in synchronized change with the EPAP). The IPAP pressure can also have a first course in this meaning, which is changed automatically or upon user selection in following cycles of the respiration.

For example, the IPAP can rise at the beginning of the inhalation and then drop or assume a maximum value or minimum value in the middle of the inhalation. Alternatively, the IPAP can also assume a maximum value at the end of the inhalation.

What is claimed is:

1. A respiratory device, wherein the device comprises a respirator having a controllable respiratory gas source and a programmable control unit and at least one sensor unit for determining pressure and/or flow of a respiratory gas, wherein the control unit controls the respiratory gas source to specify a first respiration pattern with respect to pressure, flow, volume, and frequency, wherein the respiratory device further comprises a first sensor unit comprising a plurality of individual sensors configured for generating and/or measuring electrical potentials and noninvasively determining an electrical impedance of lungs of a patient, a second sensor unit configured for noninvasively determining a carbon dioxide supply, and a third sensor unit configured for noninvasively determining an oxygen supply of the patient, wherein the control unit evaluates (i) measured values of the first sensor unit to determine an instantaneous ventilation of the lungs during respiration using the first respiration pattern, (ii) measured values of the second sensor unit to determine an instantaneous carbon dioxide supply, and (iii) measured values of the third sensor unit to determine an instantaneous oxygen supply, and wherein the control unit evaluates (i) the sensor measured values of the first sensor unit to determine a resulting ventilation of the lungs during respiration using a second respiration pattern, (ii) the sensor measured values of the second sensor unit to determine the resulting carbon dioxide supply during the respiration using the second respiration pattern, and (iii) the sensor measured values of the third sensor unit to determine the resulting oxygen supply during the respiration using the second respiration pattern and compares the instantaneous ventilation to the resulting ventilation, and wherein information about the ventilation of the lung, the oxygen supply, and the carbon dioxide supply are used for controlling and regulating the respiration, and wherein the control unit controls the respiratory gas source to specify the second respiration pattern, which is different from the first respiration pattern with respect to pressure and/or flow and/or volume and/or frequency, if (1) the first sensor unit indicates an unchanged EIT (Electrical Impedance Tomography) summation signal in response to the first respiration pattern and an elevated EIT change frequency, such that the second respiration pattern has an elevated mandatory frequency in comparison to the first respiration pattern; and/or (2) the first sensor unit indicates an unchanged EIT summation signal in response to the first respiration pattern and a reduced amount for the carbon dioxide supply, such that the second respiration pattern has an elevated mandatory frequency in comparison to the first respiration pattern; and/or (3) the first sensor unit indicates an EIT summation signal reduced in response to the first respiration pattern and a reduced amount for the carbon dioxide supply, such that the second respiration pattern has an elevated mandatory frequency in comparison to the first respiration pattern and/or an elevated tidal volume and/or an elevated pressure assistance; and/or (4) the first sensor unit indicates an unchanged EIT summation signal in response to the first respiration pattern and an elevated amount for the carbon dioxide supply, such that the second respiration pattern has a changed EPAP pressure or course in comparison to the first respiration pattern; and/or (5) the first sensor unit indicates an unchanged EIT summation signal in response to the first respiration pattern and an elevated measure for the carbon dioxide supply, such that the second respiration pattern has an elevated mandatory frequency in comparison to the first respiration pattern if an EIT change frequency is reduced; and/or (6) the first sensor unit indicates a reduced EIT summation signal in response to the first respiration pattern and a reduced EIT change frequency and an elevated amount for the carbon dioxide supply, such that the second respiration pattern has an elevated mandatory frequency and/or an elevated tidal volume and/or an elevated pressure assistance in comparison to the first respiration pattern; and/or (7) the first sensor unit indicates an EIT summation signal elevated in response to the first respiration pattern and/or a reduced EIT change frequency and a reduced amount for the oxygen supply, such that the second respiration pattern has an elevated frequency in comparison to the first respiration pattern and/or an at least short-term elevation of inspiration time and/or an adaptation of PEEP and/or a change of the respiration pattern.

2. The respiratory device of claim 1, wherein the control unit controls the respiratory gas source to specify the first respiration pattern and stores resultant first measured values of the at least one sensor unit and then controls the respiratory gas source to specify the second respiration pattern and stores resultant second sensor measured values of the at least one sensor unit and compares the first sensor measured values to the second sensor measured values.

3. The respiratory device of claim 1, wherein the device further comprises at least one storage unit which communicates with the control unit and in which at least standard values and/or limiting values for the carbon dioxide supply and for the oxygen supply are stored.

4. The respiratory device of claim 3, wherein the control unit controls the respiratory gas source to specify the second respiration pattern which is different from the first respiration pattern with respect to pressure and/or flow and/or volume and/or frequency, if the sensor measured values of the instantaneous carbon dioxide supply and/or the sensor measured values of the instantaneous oxygen supply deviate from the standard values thereof and/or the limiting values thereof are at least reached.

5. The respiratory device of claim 3, wherein standard values and limiting values for a ventilation of the lungs are stored in the storage unit and the control unit controls the respiratory gas source to specify the second respiration pattern, which is different from the first respiration pattern with respect to pressure and/or flow and/or volume and/or frequency, if the instantaneous ventilation deviates from the standard values thereof and the limiting values thereof are at least reached.

6. The respiratory device of claim 1, wherein the control unit controls the respiratory gas source to specify the second respiration pattern in such a way that the resulting ventilation of the lungs is improved in relation to the instantaneous ventilation.

7. The respiratory device of claim 1, wherein the control unit controls the respiratory gas source to specify the second respiration pattern, which is different from the first respiration pattern with respect to pressure and/or flow and/or volume and/or frequency, so that sensor measured values of the resulting carbon dioxide or oxygen supply at least approximate target values.

8. The respiratory device of claim 1, wherein the control unit controls the respiratory gas source to specify the second respiration pattern, which is different from the first respiration pattern with respect to pressure and/or flow and/or volume and/or frequency, if sensor measured values of the instantaneous ventilation and/or of the instantaneous oxygen supply deviate from standard values thereof and limiting values thereof are at least reached.

9. The respiratory device of claim 1, wherein (1) applies.
10. The respiratory device of claim 1, wherein (2) applies.
11. The respiratory device of claim 1, wherein (3) applies.
12. The respiratory device of claim 1, wherein (4) applies.
13. The respiratory device of claim 1, wherein (5) applies.
14. The respiratory device of claim 1, wherein (6) applies.
15. The respiratory device of claim 1, wherein (7) applies.

16. The respiratory device of claim 1, wherein the control unit controls the respiratory gas source to specify a first PEEP and stores resulting first sensor measured values of at least one sensor unit, then controls the respiratory gas source to specify a second PEEP and stores resulting second sensor measured values of the at least one sensor unit and then compares the first sensor measured values to the second sensor measured values.

17. The respiratory device of claim 1, wherein the control unit controls the respiratory gas source to specify the first respiration pattern, in which an EPAP pressure has a first value or a first course, wherein the first sensor unit determines the resulting ventilation of the lungs, the second sensor unit determines the carbon dioxide supply and/or the third sensor unit determines the oxygen supply of the patient, wherein the control unit stores the sensor measured values which result during the respiration using the first pattern, wherein the control unit controls the respiratory gas source to specify the second respiration pattern, in which the EPAP pressure has a second value or a second course, wherein the first sensor unit determines the resulting ventilation of the lungs, the second sensor unit determines the carbon dioxide supply and the third sensor unit determines the oxygen supply of the patient, wherein the control unit stores the sensor measured values which result during the respiration using the second pattern, and wherein the control unit compares the sensor measured values which result after application of the first respiration pattern to the sensor measured values which result after application of the second respiration pattern.

18. A respiratory device, wherein the device comprises a respirator having a controllable respiratory gas source and a programmable control unit and at least one sensor unit for determining pressure and/or flow of a respiratory gas, wherein the control unit controls the respiratory gas source to specify a first respiration pattern with respect to pressure, flow, volume, and frequency, wherein the respiratory device further comprises a first sensor unit comprising a plurality of individual sensors configured for generating and/or measuring electrical potentials and noninvasively determining an electrical impedance of lungs of a patient, a second sensor unit configured for noninvasively determining a carbon dioxide supply, and a third sensor unit configured for noninvasively determining an oxygen supply of the patient, wherein the control unit evaluates (i) measured values of the first sensor unit to determine an instantaneous ventilation of the lungs during respiration using the first respiration pattern, (ii) measured values of the second sensor unit to determine an instantaneous carbon dioxide supply, and (iii) measured values of the third sensor unit to determine an instantaneous oxygen supply, and wherein the control unit evaluates (i) the sensor measured values of the first sensor unit to determine a resulting ventilation of the lungs during respiration using a second respiration pattern, (ii) the sensor measured values of the second sensor unit to determine the resulting carbon dioxide supply during the respiration using the second respiration pattern, and (iii) the sensor measured values of the third sensor unit to determine the resulting oxygen supply during the respiration using the second respiration pattern and compares the instantaneous ventilation to the resulting ventilation, and wherein information about the ventilation of the lung, the oxygen supply, and the carbon dioxide supply are used for controlling and regulating the respiration, and wherein the control unit monitors at least one sensor signal for errors in that if an instantaneous sensor signal reaches limiting values, it is compared to another instantaneous sensor signal to detect an inaccuracy and/or monitors a first sensor signal for errors in that the control unit at least temporarily compares the first sensor signal to a signal of the at least one sensor unit for determining pressure and/or flow of a respiratory gas.

* * * * *